(12) United States Patent
Fankhauser et al.

(10) Patent No.: US 6,384,242 B1
(45) Date of Patent: May 7, 2002

(54) GERANIC ACID DERIVATIVES

(75) Inventors: Peter Fankhauser, Meyrin; Paul Hanselmann; Barry Jackson, both of Brig-Glis, all of (CH)

(73) Assignees: Firmenich SA, Geneva; Lonza AG, Basil, both of (CH)

( * ) Notice: Subject to any disclaimer, the term of this patent is extended or adjusted under 35 U.S.C. 154(b) by 0 days.

(21) Appl. No.: 09/786,279

(22) PCT Filed: Aug. 24, 1999

(86) PCT No.: PCT/IB99/01463

§ 371 Date: Jun. 21, 2001

§ 102(e) Date: Jun. 21, 2001

(87) PCT Pub. No.: WO00/14080

PCT Pub. Date: Mar. 16, 2000

(30) Foreign Application Priority Data

Sep. 3, 1998 (EP) .............................. 98116634

(51) Int. Cl.⁷ ............................................. C07D 305/12
(52) U.S. Cl. ................. 549/328; 554/121; 554/132; 554/161; 562/510; 560/126
(58) Field of Search .......................... 549/328; 554/121, 554/132, 161; 562/510; 560/126

(56) References Cited

U.S. PATENT DOCUMENTS 2,585,223 A * 2/1952 Caldwell et al.
3,887,625 A * 6/1975 Schulte et al.

OTHER PUBLICATIONS

FKYERAT A et al Tetrahedron vol. 7 #7 p. 2023–28 1996.*

* cited by examiner

*Primary Examiner*—Paul J. Killos
(74) *Attorney, Agent, or Firm*—Fisher, Christen & Sabol

(57) ABSTRACT

4-Methyl-4-(4-mlthylpent-3-en-1-yl)-2-oxetanone of formula (1):

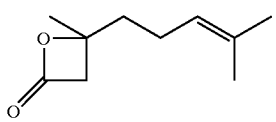

I or its oligomer is an intermediate product for the preparation of a series of geranic acid derivatives, which are important synthetic building blocks in the preparation of perfumes and fragrances.

14 Claims, No Drawings

GERANIC ACID DERIVATIVES

This application is a 371 national stage application of International Application PCT/IB99/01463, filed on Aug. 24, 1999, which has benefit of European Patent Application 98116634.1, filed on Sep. 3, 1998.

BACKGROUND OF THE INVENTION

Field of the Invention

The invention relates to 4-methyl-4-(methylpent-3-en-1-yl)-2-oxetanone of the formula:

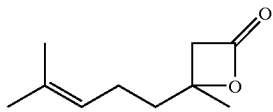

as a new intermediate product for the preparation of various geranic acid derivatives.

The invention also relates to a process for the preparation of 3-hydroxycitronellic acid derivatives of the general formula:

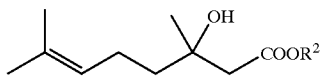

where $R^2$ is hydrogen or an alkyl group, a process for the preparation of cyclogeranic derivatives of the general formula:

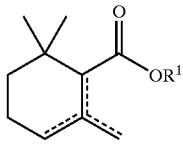

where $R^1$ is hydrogen or an alkyl group, a process for the preparation of geranic acid derivatives of the formula:

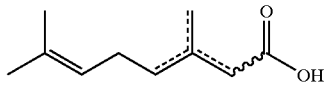

and a process for the preparation of 2,6-dimethyl-hepta-1,5-diene.

4-Methyl-4-(4-methylpent-3-en-1-yl)-2-oxetanone and the aforementioned compounds prepared therefrom according to the invention are important synthetic building blocks in the preparation of perfumes and fragrances.

BROAD DESCRIPTION OF THE INVENTION

The object of the invention is to provide simple, commercially feasible access to the aforementioned synthetic building blocks.

The object is achievable by the provision of the intermediate product 4-methyl-4-(4-methylpent-3-en-1-yl)-2-oxetanone of the formula:

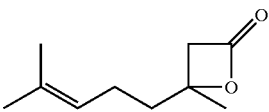

4-Methyl-4-(4-methylpent-3-en-1-yl)-2-oxetanone of the formula I is prepared according to the invention by conversion of 6-methyl-5-hepten-2-one with ketene in the presence of a catalyst.

DETAILED DESCRIPTION OF THE INVENTION

6-Methyl-5-hepten-2-one is a commercially available compound. Ketene is obtained in a known manner, usually directly by cracking diketene, at temperatures of over 300° C.

Lewis acids are suitable as catalysts. The conventional Lewis acids known to those skilled in the art can be used, e.g., zinc chloride, titanium tetrachloride, aluminum chloride, boron trifluoride or boron trifluoride etherate. Good results are obtained with boron trifluoride etherate.

The Lewis acids are advantageously used in an amount of 0.1 mol percent to 5 mol percent relative to the 6-methyl-5-hepten-2-one used.

It is possible to carry out conversion in the absence of a solvent, but an inert solvent is advantageously used; for example, halogenated hydrocarbons such as methylene chloride or carbon tetrachloride have proved successful.

Usually, the ketene is added, and the reaction takes place at a temperature of −30° C. to 40° C., preferably −30° C. to 0° C.

Depending on the temperature gradient of the ketene addition, the 4-methyl-4-(4-methylpent-3-en-1-yl)-2-oxetanone can. form an oligomer of the formula:

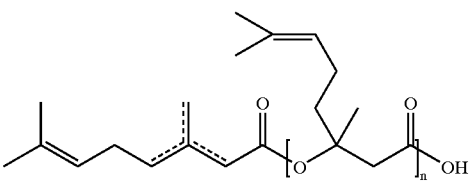

where n is usually a number ≧1. At low temperatures of −30° C. to 0° C., 4-methyl-4-(4-methylpent-3-en-1-yl)-2-oxetanone of the formula I is generally formed, whereas temperatures of 0° C. to 40° C. generally give rise to the oligomer of the formula V.

The desired lactone can be isolated in pure form by methods conventional to the skilled worker, e.g. by removing the ketene and the excess solvent and finally by distillation, e.g. in a thin-film evaporator.

To prepare the 3-hydroxycitronellic acid derivatives of the general formula

where $R^2$ is hydrogen or an alkyl group, the 4-methyl-4-(4-methylpent-3-en-1-yl)-2-oxetanone of the formula

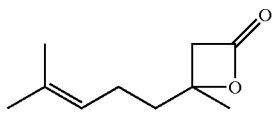

is esterified with an alcohol of the formula

R²OH                                                                                  IV where R² has the aforesaid meaning, or hydrolysed with a base to form the acid.

In the following, alkyl group is taken to mean a straight-chain or branched alkyl group with 1 to 6 C atoms, which can optionally contain one or more substituents from the series $C_{1-4}$ alkyl or phenyl. Preferably, R² stands for methyl, ethyl, n-propyl, i-propyl, n-butyl, i-butyl, t-butyl or benzyl.

Esterification is carried out with an alcohol of the formula

R²OH                                                                                  IV where R² has the aforesaid meaning, advantageously in the presence of an alkali alcoholate.

In the alkali alcoholate, the alcoholate part advantageously corresponds to the R² OH alcohol used.

Preferably, the sodium or potassium alcoholates of the R² OH alcohols in question are used.

Conversion is usually carried out at a temperature of 0° C. to 30° C. The alcohol, used in excess, acts as a solvent.

The resulting esters can be isolated by methods conventional to the skilled worker and obtained in pure form, e.g. by distillation.

Hydrolysis is carried out with a base to form the acid.

The selection of the base is in itself not critical and the conventional base hydrolysis methods can be used. Suitable bases are aqueous solutions of alkali or alkaline-earth hydroxides; an aqueous sodium hydroxide solution is particularly suitable.

Addition of a catalyst is not necessary for hydrolysis, but can be advantageous in accelerating the reaction.

In this case, the conventional phase-transfer catalysts known to those skilled in the art are suitable, e.g. quaternary ammonium compounds. Good results can be obtained using tributylbenzylammonium chloride, for example.

Base hydrolysis is advantageously carried out at a temperature in the range from 20° C. to 80° C. The 3-hydroxycitronellic acid can be isolated from the reaction mixture e.g. by extraction of the acidified aqueous phase using a suitable organic solvent, e.g. diethyl ether.

To prepare the cyclogeranic acid derivatives of the general formula

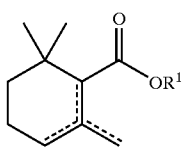

where $R_1$ is hydrogen or an alkyl group, the 4-methyl-4-(4-methylpent-3-en-1-yl)-2-oxetanone of the formula I is converted in the presence of a strong acid at a temperature of 20° C. to 100° C.

The broken line in formula II is intended to show that the double bond can either be in the α-position or β-position relative to the carboxyl group or in the exo-position, and that a mixture of the compounds

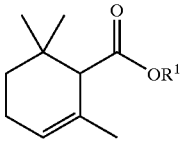

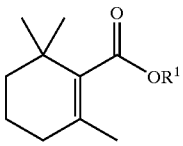

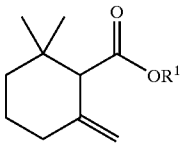

where $R_1$ has the aforesaid meaning, is usually produced as a reaction product.

The starting product for the ring closure can either be the 4-methyl-4-(4-methylpent-3-en-1-yl)-2-oxetanone of the formula I or the polymer of the formula V.

According to the invention, cyclisation takes place in the presence of a strong acid.

Sulfuric acid or a mixture of the aforementioned acid with formic acid or acetic acid can be used as a strong acid.

The reaction temperature is advantageously selected in a range from 20° C. to 100° C.

The cyclogeranic acid derivatives of the general formula II can be isolated from the reaction mixture by methods conventionally used by skilled workers and optionally further purified by distillation.

If the conversion of the 4-methyl-4-(4-methylpent-3-en-1-yl)-2-oxetanone of the formula I is carried out under comparatively less acid conditions, the geranic acid derivatives of the following formula are produced:

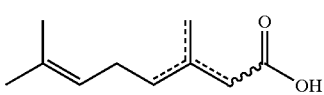

The broken line is intended to show that various isomers of the geranic acid can be produced as a reaction product. The wavy line indicates that the geranic acid can be present as either an E-isomer or a Z-isomer. The preferred geranic acid derivative is the (E)- or (Z)-geranic acid of the formula

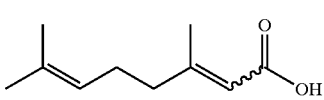

However, it has been shown that the acidity and temperature of the reaction mixture are the decisive factors in determining whether cyclogeranic acid derivatives of the formula II are produced or whether the reaction stops at the preliminary stage of the geranic acid derivatives of the formula VIII.

To promote the production of the geranic acid derivatives of the formula VIII, it has proved advantageous to use a mineral acid such as sulfuric acid in the presence of an organic solvent.

Good results can be obtained using protonated N,N-dimethyl formamide. Conversion can advantageously be carried out at a temperature of 0° C. to 60° C. This conversion generally results in a mixture of isomers which, however, can be substantially converted into the (E)- and/or (Z)-geranic acid of the formula VIIIa using p-toluenesulfonyl chloride/pyridine by the method used by Fujisawa et al in Bull. Soc. Chem. Jpn. 55 (1982) 3555–3559.

According to a further embodiment of the invention, the 4-methyl-4-(4-methylpent-3-en-1-yl)-2-oxetanone of the formula I can be converted into 2,6-dimethyl-hepta-1,5-diene of the formula

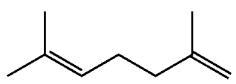

VII by pyrolysis at a temperature of 100° C. to 250° C.

Preferably, the 4-methyl-4-(4-methylpent-3-en-1-yl)-2-oxetanone is pyrolysed under the aforementioned conditions, preferably at 180° C. to 220° C. Under these conditions, a very good yield of the end product can be obtained.

The following examples will explain the invention further.

EXAMPLES

1a. Preparation of 4-Methyl-4-(4-methylpent-3-en-1-yl)-2-oxetanone 128.8 g (1.0 mol) of 6-methyl-5-hepten-2-one were dissolved in 516 g of dichloromethane in an $N_2$ atmosphere. The solution was cooled to −19° C. 0.71 g of boron trifluoride etherate (0.5 mol % relative to 6-methyl-5-hepten-2-one) were then added and ketene gas was metered in over a period of 4 h. The temperature ranged between −12° C. and −14° C. The ketene gas was drawn directly from a diketene cracker: approx. 1.25 mol of ketene were generated from 55 ml of diketene and used. The solution was stirred overnight at −15° C., during which time an $N_2$ stream was passed through the solution to remove excess ketene. Finally, 350 mg (2.5 mmol) of urotropine were added, the solution stirred again for 30 minutes and heated to 0° C. The solvent was then evaporated off at 15 mbar and 20° C. The crude product was obtained in the form of an orange solution. Distillation by way of a thin-film evaporator at 1–2 mbar and with an overhead temperature of 88° C. yielded 136 g (80.9%) of the title product.

$^1$-H-NMR ($CDCl_3$, 400 MHz): δ5.09 (t, =CH, J=6 Hz); 3.22 (d, CH, J=16 Hz); 3.10 (d, CH, J=16 Hz); 2.10 (m, $CH_2$); 1.86 (m, $CH_2$); 1.69 (s, $CH_3$); 1.62 (s, $CH_3$); 1.57 (s, $CH_3$); GLC-MS: m/e 168 (2%), 109 (11%), 93 (6%), 81 (42%), base peak 69 (100%), 55 (9%), 53 (9%), 44 (15%), 43 (18%), 41 (70%), 39 (24%).

1b. Preparation of the Oligomer of 4-Methyl-4-(4-methylpent-3-en-1-yl)-2-oxetanone 0.2 g of conc. sulfuric acid was added dropwise to 20 g (0.118 mol) of 4-methyl-4-(4-methylpent-3-en-1-yl)-2-oxetanone at 10° C. so that the temperature remained below 28° C. After the exothermic reaction had subsided, the reaction mixture was stirred for 7 h at 25° C., resulting in a slightly viscous solution. Titration with (tetrabutylammonium hydroxide (TBAH) in methanol): 450 mequiv/mol monomer weight.

IR (film): 2500–3400 $cm^{-1}$ (COOH/OH), 1733 $cm^{-1}$ (C=O), 1711 $cm^{-1}$, 1647 $cm^{-1}$ (unsat. C=O).

2a. Preparation of α- and β-cyclogeranic Acid ex 4-Methyl-4-(4-methylpent-3-en-1-yl)-2-oxetanone 5.0 g (27.5 mmol) of 4-methyl-4-(4-methylpent-3-en-1-yl)-2-oxetanone were added to a solution of 11.5 g of acetic acid and 0.9 g of sulfuric acid (98%) over a period of 5 mins so that the temperature did not exceed 35° C. The reaction mixture was then heated to 90° C. and held at this temperature for 7 h. The reaction mixture was then cooled to 20° C., diluted with 50 ml of water and extracted with 50 ml of a 1:1 mixture of petroleum ether/diethyl ether. The organic phase was washed with 20 ml of water and then extracted with 25.9 g of 5% aqueous NaOH. After acidification of the extract with 36 ml of 1N HCl, extraction was carried out again with 150 ml of diethyl ether. The organic phase was evaporated (18 mbar, 50° C.), after which 2.77 g of the title product were obtained as a viscous oil. Distillation of the oil in a bulb tube (14 mbar, 185° C.) yielded 1.11 g of colourless oil, out of which the product slowly crystallised.

According to GC analysis, the content of α- and β-cyclogeranic acid was 40% and 28% respectively.

IR (film): 1400–3400 $cm^{-1}$ (—COOH), 1703 $cm^{-1}$ (—C=O), 1645 $cm^{-1}$ (—C=C—).

2b. Preparation of α- and β-cyclogeranic Acid ex Oligomer of the Formula V 5.0 g of the oligomer prepared according to example 1b were added to a solution of 11.5 g of acetic acid and 0.9 g of sulfuric acid (98%) over a period of 5 mins so that the temperature did not exceed 35° C. The reaction mixture was then heated to 90° C. and held at this temperature for 18 h. The reaction mixture was then cooled to 20° C., diluted with 50 ml of water and extracted with 50 ml of a 1:1 mixture of petroleum ether/diethyl ether. The organic phase was washed with 20 ml of water and then extracted with 25.9 g of 5% aqueous NaOH. After acidication of the extract with 36 ml of 1N HCl, extraction was carried out again with 150 ml of diethyl ether. The organic phase was evaporated (18 mbar, 50° C.), after which 1.83 g of the title product were obtained as a viscous oil. Distillation of the oil in a bulb tube (17–18 mbar, 185° C.) yielded 1.18 g of yellow oil, out of which the product slowly crystallised.

According to GC analysis, the content of α- and β-cyclogeranic acid was 47% and 30% respectively.

IR (film): 1400–3400 $cm^{-1}$ (-COOH), 1703 $cm^{-1}$ (—C=O), 1645 $cm^{-1}$ (—C=C—).

3. Preparation of 3-hydroxycitronellic Acid [(+−)-3-Hydroxy-3,7-oct-6-enoic Acid]

48.99 g (0.259 mol) of 4-methyl-4-(4-methylpent-3-en-1-yl)-2-oxetanone, 180 ml of NaOH 2N and 0.49 g of tributylbenzylammonium chloride (PTC catalyst) were vigorously stirred together, whereupon the reaction temperature rose to 51° C. The mixture was further stirred at this temperature for 2.75 h, then cooled to 20° C. and stirred again overnight. The reaction mixture was extracted with 2×100 ml of diethyl ether. The aqueous phase was separated, the organic phase acidified with 390 ml of 1N HCl and the organic phase separated off. The remaining aqueous phase was extracted with 10 ml of diethyl ether. The organic phases were combined, dried over sodium sulfate and filtered. The filtrate was concentrated at 20 mbar and 30° C. 42.7 g (83.4%) of the title product were obtained in the form of a yellow oil.

1-H-NMR (CDCl$_3$, 400 MHz):β5.95 (s, br, OH, COOH); 5.10 (t, CH, J=6 Hz); 2.58 (d, CH, J=16 Hz); 2.50 (d, CH, J=16 Hz); 2.06 (m, CH$_2$); 1.68 (s, CH$_3$); 1.61 (s, CH$_3$); 1.58 (m, CH$_2$); 1.30 (s, CH$_3$).

4. Preparation of (+−)-3,7-Dimethyl-3-hydroxy-oct-6-enoic Acid Methyl Ester 0.69 g of Na metal were dissolved in 200 g of methanol and cooled to 10° C. 50.47 g (0.279 mol) of 4-methyl-4-(4-methylpent-3-en-1-yl)-2-oxetanone were then added over a period of 17 mins, during which time the temperature rose to 16° C. Next, the mixture was stirred at 20° C. for 1.2 h and then acidified with 4.14 g (30 mmol) of sodium hydrogen sulfate. After being stirred for a further 1.7 h at 20° C., the suspension was filtered. The filtrate was concentrated (80 mbar, 40° C.). The residue (56.56 g) was then fractionated at 1 mbar, and the main fraction distilled at 95° C. to 97° C. 49.52 g (87.1%) of the title product were obtained in the form of an oil.

1-H-NMR (CDCl$_3$, 400 MHz):β5.09 (t, =CH, J=6 Hz); 3.71 (s, OCH$_3$); 3.40 (s, br, OH); 2.54 (d, CH, J=16 Hz); 2.45 (d, CH, J=16 Hz); 2.06 (m, CH$_2$); 1.69 (s, CH$_3$); 1.61 (s, CH$_3$); 1.54 (m, CH$_2$); 1.25 (s, CH$_3$).

5. Preparation of a Mixture of (E)- and (Z)-geranic Acid 2 g of sulfuric acid (conc.) were dissolved in 20 ml of dry N,N-dimethyl formamide while being cooled. 10 g (0.059 mol) of 4-methyl-4-(4-methylpent-en-1-yl)-2-oxetanone were added dropwise to this solution at 20° C. to 25° C. over a period of 5 minutes. The solution was heated to 50° C. to 55° C. over a period of 15 minutes, held at this temperature for 7 h and cooled to 20° C. The solution was then introduced into 50 ml of water. The emulsion was extracted with 3×30 ml of toluene. The organic phase was washed with 3×20 ml, dried with sodium sulfate, filtered and, finally, concentrated at 20 mbar and 45° C. 8.46 g of crude product were obtained and distilled in a bulb tube at 20 mbar and 215° C. 7.54 g of product were obtained in the form of a yellow oil.

In a second step according to the method used by Fujisawa et al in Bull. Soc. Chem. Jpn. 55 (1982) 3555–3559, 3.37 g of this product were first dissolved in 30 ml of pyridine and mixed with 4.2 g (22 mmol) of p-toluenesulfonyl chloride. The reaction mixture was stirred at 30° C. for 1 h. 1.8 g (10 mmol) of water were then added. The mixture was stirred again at 30° C. for half an hour and then mixed with 60 g of 6N HCl. The reaction mixture was first extracted with 3×20 ml of diethyl ether, and the resulting organic phase extracted with 3×20 ml of 3N NaOH.

Re-acidification of the aqueous phase with 6N HCl to pH 1, renewed extraction with 3×20 ml of diethyl ether, drying of the organic phase with sodium sulfate and concentration yielded 2.8 g of crude title product. According to GLC analysis, the product contained 29% (Z)-geranic acid and 52% (E)-geranic acid.

6. Preparation of 2,6-Dimethyl-hepta-1,5-diene 22.0 g (111 mmol) of 4-methyl-4-(4-methylpent-3-en-1-yl)-2-oxetanone were added dropwise to a reaction vessel preheated to 200° C. The gaseous reaction products were fractionated in a Vigreux column. 14.21 g (96.2%) of the title product were thus yielded.

1-H-NMR (CDCl$_3$, 400 MHz):β5.11 (t, =CH, J=6 Hz); 4.70 (s, =CH); 4.67 (s, =CH); 2.54 (d, CH, J=16 Hz); 2.11 (m, CH$_2$); 2.03 (m, CH$_2$); 1.72 (s, CH$_3$); 1.69 (s, CH$_3$); 1.61 (s, CH$_3$).

What is claimed is:

1. 4-Methyl-4-(4-methylpent-3-en-1-yl)-2-oxetanone of the formula

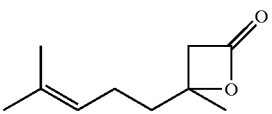

I or its oligomer of the formula

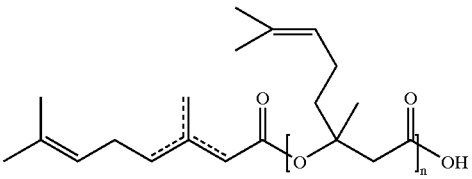

V where n>1.

2. A process for the preparation of 4-methyl-4-(4-methylpent-3-en-1-yl)-2-oxetanone of the formula of claim 1 or its oligomer of the formula V, claim 1 characterised in that 6-methyl-5-hepten-2-one is converted with ketene in the presence of a catalyst.

3. A process according to claim 2, characterised in that a Lewis acid is used as a catalyst.

4. The process according to claim 3, wherein the conversion is carried out at a temperature between −30° C. and 40° C. in the presence of an inert solvent.

5. A process for the preparation of 3-hydroxycitronellic acid derivatives of the general formula

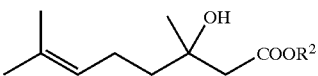

III where $R^2$ is hydrogen or an alkyl group, characterised in that the 4-methyl-4-(4-methylpent-3-en-1-yl)-2-oxetanone is either esterified with an alcohol of the formula

 IV where $R^2$ has the aforesaid meaning, or hydrolysed to form the acid.

6. A process according to claim 5, characterised in that conversion to the ester is carried out in the presence of an alkali alcoholate at a temperature between 0° C. and 30° C.

7. The process according to claim 5, wherein the conversion to the acid is carried out using an alkali-earth hydroxide as a base.

8. A process for the preparation of cyclogeranic acid derivatives of the general formula

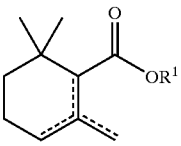

II where $R^1$ is hydrogen or an alkyl group, characterised in that the 4-methyl-4-(4-methylpent-3-en-1-yl)-2-oxetanone of the formula claim 1 is reacted in the presence of a strong acid.

9. The process according to claim 8, wherein sulfuric acid is used as a strong acid and is worked at a temperature of 20° C. to 100° C.

10. A process for the preparation of geranic acid derivatives of the formula

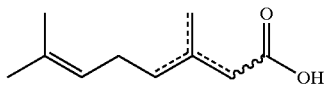   VIII characterised in that the 4-methyl-4-(4-methylpent-3-en-1-yl)-2-oxetanone of the formula claim 1 is reacted with a mineral acid in the presence of an organic solvent.

11. A process for the preparation of 2,6-dimethyl-hepta-1,5-diene of the formula

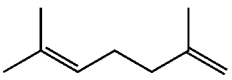   VII characterised in that the 4-methyl-4-(4-methylpent-3-en-1-yl)-2-oxetanone of the formula claim 1 is pyrolysed at a temperature of 100° C. to 250° C.

12. The process according to claim 2, wherein the conversion is carried out at a temperature between −30° C. and 40° C. in the presence of an inert solvent.

13. The process according to claim 5, wherein the conversion to the acid is carried out using an alkali or alkaline-earth hydroxide as a base in the presence of a phase transfer catalyst.

14. The process according to claim 8, wherein the sulfuric acid, mixed with formic acid or acetic acid, is used as a strong acid and is worked at a temperature of 20° C. to 100° C.

* * * * *